United States Patent
Eichert et al.

(10) Patent No.: US 12,071,521 B2
(45) Date of Patent: Aug. 27, 2024

(54) METHOD, DEVICE AND USE FOR REPROCESSING SUBSTANTIALLY POLYALKYLENE TEREPHTHALATE

(71) Applicant: Rittec Umwelttechnik GmbH, Lüneburg (DE)

(72) Inventors: Carsten Eichert, Lüneburg (DE); Esther Brepohl, Lüneburg (DE); Stephan Scholl, Lüneburg (DE); Lars Biermann, Lüneburg (DE)

(73) Assignee: RITTEC UMWELTTECHNIK GMBH, Lüneburg (DE)

( * ) Notice: Subject to any disclaimer, the term of this patent is extended or adjusted under 35 U.S.C. 154(b) by 0 days.

(21) Appl. No.: 17/275,822

(22) PCT Filed: Sep. 4, 2019

(86) PCT No.: PCT/EP2019/073598
§ 371 (c)(1),
(2) Date: Mar. 12, 2021

(87) PCT Pub. No.: WO2020/053051
PCT Pub. Date: Mar. 19, 2020

(65) Prior Publication Data
US 2021/0253823 A1    Aug. 19, 2021

(30) Foreign Application Priority Data
Sep. 12, 2018 (DE) ............... 10 2018 122 210.6

(51) Int. Cl.
*C08J 11/24* (2006.01)
*B29B 17/02* (2006.01)
(Continued)

(52) U.S. Cl.
CPC ............ *C08J 11/24* (2013.01); *B29B 17/02* (2013.01); *B29B 17/0412* (2013.01);
(Continued)

(58) Field of Classification Search
CPC ....... C08J 11/24; C08J 2367/02; B29B 17/02; B29B 17/0412; B29B 2017/0296;
(Continued)

(56) References Cited

U.S. PATENT DOCUMENTS 3,120,561 A     2/1964  Chambret
3,544,622 A  *  12/1970 England ................. C08J 11/16
                                                     562/483
(Continued)

FOREIGN PATENT DOCUMENTS

CN         1090569 A     8/1994
DE       69316545 T2     7/1998
(Continued)

OTHER PUBLICATIONS

Patterson, Joan Diana. "Continuous Depolymerization of Poly (ethylene terephthalate) via Reactive Extrusion.", retrieved from repository.lib.ncsu.edu (Year: 2007).*
(Continued)

*Primary Examiner* — Frances Tischler
(74) *Attorney, Agent, or Firm* — Dickinson Wright PLLC

(57) ABSTRACT

A method and a device for reprocessing waste products containing substantially polyalkylene terephthalate, particularly polyethylene terephthalate and/or polybutylene terephthalate, in a continuous process by means of depolymerizing is provided. A solid alkali hydroxide and/or alkali earth hydroxide, particularly sodium hydroxide, is added to the waste products for producing a reaction mixture, suitable for recycling multilayer systems and colored material nearly entirely chemically into the starting materials at a high throughput and high quality, in order to be able to produce new polyalkylene terephthalate products from the recycling products without limitation. An alkylene glycol is additionally added to the reaction mixture as a reactant, wherein the (Continued)

alkylene glycol is an alkylene glycol produced as a product of the intended depolymerizing, particularly MEG. No further reactive components are added to the reaction mixture.

15 Claims, 1 Drawing Sheet

(51) Int. Cl.
    *B29B 17/04*     (2006.01)
    *B29K 67/00*     (2006.01)

(52) U.S. Cl.
    CPC . *B29B 2017/0296* (2013.01); *B29K 2067/003* (2013.01); *C08J 2367/02* (2013.01)

(58) Field of Classification Search
    CPC ............ B29B 2017/0015; B29B 7/007; B29K 2067/003; B29K 2067/006; C07C 51/09; C07C 63/26; Y02W 30/62
    See application file for complete search history.

(56) References Cited

U.S. PATENT DOCUMENTS

| | | | |
|---|---|---|---|
| 3,720,448 A | 3/1973 | Allen et al. | |
| 3,952,053 A | 4/1976 | Brown, Jr. et al. | |
| 4,355,175 A | 10/1982 | Pusztaszeri | |
| 4,542,239 A | 9/1985 | Lamparter et al. | |
| 4,578,502 A | 3/1986 | Cudmore | |
| 5,395,858 A | 3/1995 | Schwartz, Jr. | |
| 6,610,392 B1 | 8/2003 | Ramesh et al. | |
| 9,475,251 B2 | 10/2016 | Shah et al. | |
| 2002/0100995 A1* | 8/2002 | Bandera | B29C 48/405 264/102 |
| 2003/0225299 A1 | 12/2003 | Yazaki | |
| 2013/0337025 A1* | 12/2013 | Le | C08G 63/88 424/401 |
| 2016/0039992 A1* | 2/2016 | Jain | C08J 11/08 521/48 |
| 2016/0136844 A1* | 5/2016 | Williams | B29B 9/12 264/101 |
| 2017/0152203 A1 | 6/2017 | Essaddam | |

FOREIGN PATENT DOCUMENTS

| | | |
|---|---|---|
| DE | 10058773 A1 | 8/2001 |
| DE | 69522479 T2 | 5/2002 |
| DE | 69714614 T2 | 4/2003 |
| EP | 1036813 A1 | 9/2000 |
| EP | 1710226 A1 | 10/2006 |
| JP | H09286744 A | 11/1997 |
| JP | H11302208 A | 11/1999 |
| JP | 2007023119 A | 2/2007 |
| JP | 2007153942 A | 6/2007 |
| JP | 2008081513 A | 4/2008 |
| WO | 9323465 A1 | 11/1993 |
| WO | 9410121 A1 | 5/1994 |
| WO | 03070376 A1 | 8/2003 |
| WO | 03104315 A1 | 12/2003 |
| WO | 2005061599 A1 | 7/2005 |
| WO | 2013014650 A1 | 1/2013 |
| WO | 2015190941 A1 | 12/2015 |

OTHER PUBLICATIONS

International Preliminary Examination Report with Translation dated Oct. 18, 2020.
International Search Report with Written Report and Translation dated Jan. 29, 2020.
Liu, Junkie, et al.; Technology for Recycling and Reusing of Plastic Wastes; China Petrochemical Press; Publication Date: May 31, 2000; pp. 163-164.
Xu, Tongkao; Practical Technology for Plastic Modifications; China Light Industry Press; Publication Date: Oct. 31, 2012; pp. 69-80.
Bergmann, Björn, et al. On-Line Monitoring of Molecular Weight Using NIR Spectroscopy in Reactive Extrusion Process. In: Macromolecular Symposia. 2013. S. 138-141.
Kaiser, K.; Schmid, M.; Schlummer, M. Recycling of polymer-based multilayer packaging: a review. Recycling. 2018.
Sinha, Vijaykumar, et al. Pet Waste Management by Chemical Recycling: A Review. In: J Polym Environ (2010) 18:8-25 9.

* cited by examiner

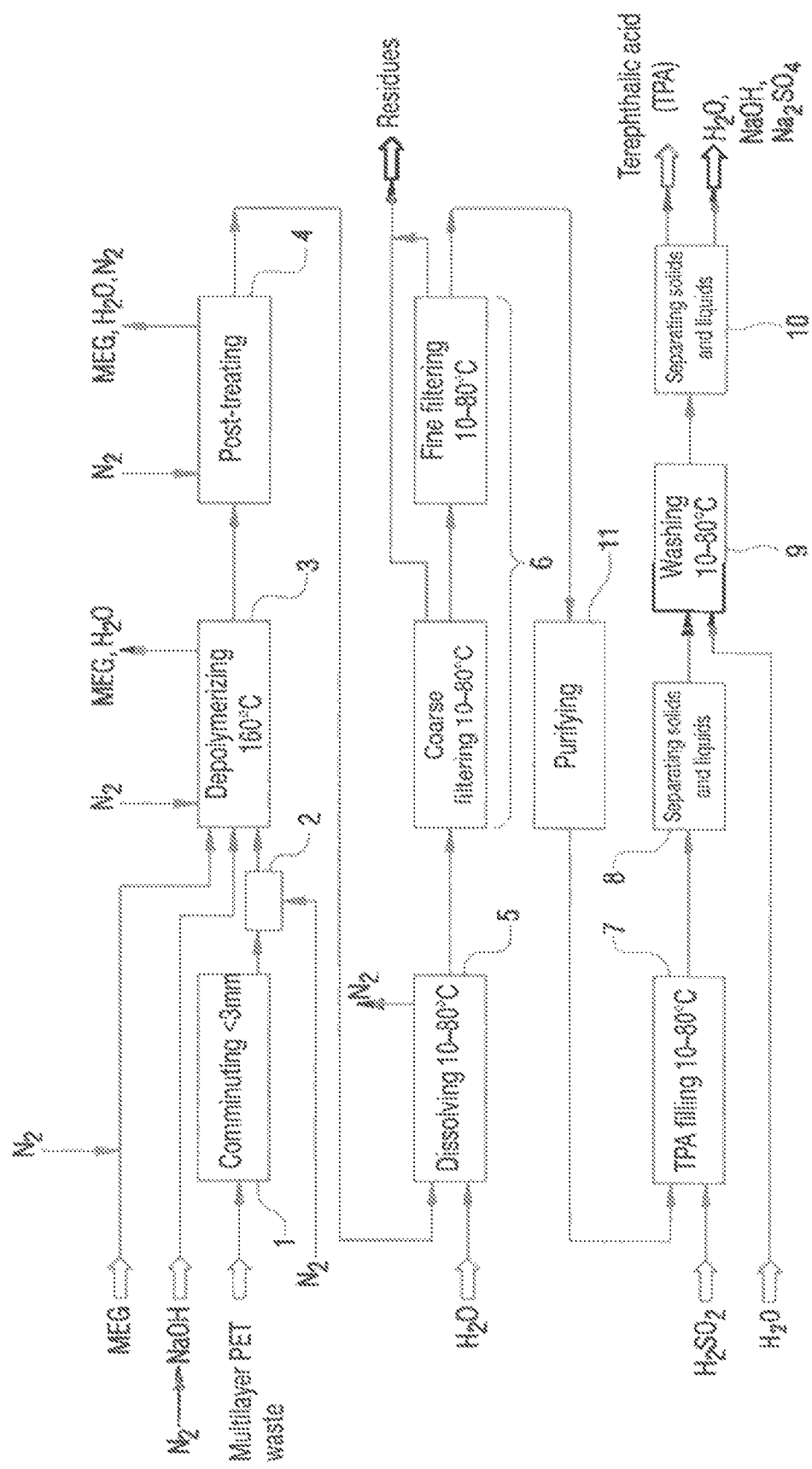

METHOD, DEVICE AND USE FOR REPROCESSING SUBSTANTIALLY POLYALKYLENE TEREPHTHALATE

TECHNICAL FIELD

The present invention relates to a method for reprocessing waste products comprising substantially polyalkylene terephthalate, particularly polyalkylene terepthalate and/or polyalkylene terephthalate, in a continuous process by means of a depolymerizing, wherein a preferably solid alkali hydroxide and/or alkali earth hydroxide, particularly sodium hydroxide, is added to the waste products for producing a reaction mixture.

The present invention further relates to a device for performing such a method.

BACKGROUND

Various methods are known for producing TPA or an intermediate of TPA from polyalkylene terephthalate and particularly from polyethylene terephthalate (PET) in the form of waste products. Said methods, however, do not process multilayered PET waste products and are neither efficient nor economically advantageous. Said methods are presented briefly below.

A method for obtaining TPA from PET waste products by means of aqueous ammonium hydroxide is described in U.S. Pat. No. 4,542,239. Both elevated pressure and elevated temperature are necessary for performing the method. Extensive safety requirements must also be fulfilled when using ammonium hydroxide.

U.S. Pat. Nos. 3,120,561 and 4,578,502 disclose the depolymerizing of PET in the presence of water or methanol by hydrolysis. A high temperature and high pressure are thereby also required for a plurality of hours in order to subsequently obtain TPA by cooling.

In U.S. Pat. No. 4,355,175, the hydrolysis of PET waste products takes place by means of diluted sulfuric acid. The solution is then treated with an alkaline solution in order to be able to separate out precipitated contaminants by filtering. TPA is obtained by adding sulfuric acid.

U.S. Pat. No. 3,952,053 describes a method for treating polyester production waste products. Sulfuric acid is thereby added first, in order to be able to subsequently remove dyes and additives. Sodium hydroxide is added to said purified intermediate product so that TPA is precipitated. The monoethylene glycol (MEG) content is recovered by distilling.

In the German patent 69714614, an aqueous, slightly alkaline solution is used at elevated temperature and elevated pressure for depolymerizing PET. For the alkaline solution, reagents from the group of bicarbonates of ammonia and alkali metals, ammonium carbamate, and urea are used. The released carbon dioxide is recycled.

In German patent 69522479, depolymerizing takes place by means of a solvent (such as water) and a wetting agent in the presence of an alkali metal or alkaline earth hydroxide at elevated temperature and elevated pressure. After filtration of the dissolved alkali metal or alkaline earth terephthalate and precipitation of TPA by means of an acid, a crystallization method is performed in order to enlarge the TPA particles.

In U.S. Pat. No. 5,395,858, PET waste products and PET waste product comprising silver (photographic and X-ray films) are depolymerized in a sodium hydroxide solution. The subsequent evaporating of the solvent leaves disodium terepthalate behind for dissolving in water and converting to TPA by means of an acid.

U.S. Pat. No. 3,544,622 describes the saponification of PET by means of sodium hydroxide and ethylene glycol at atmospheric pressure and at least 150° C. Said depolymerizing takes place batchwise in a stirrer vessel while simultaneously evaporating the ethylene glycol. The disodium terephthalate is also converted to TPA by means of an acid.

In U.S. Pat. No. 6,720,448 B2, PET is converted at elevated temperature without water, for example in ethylene glycol, by means of a salt, said salt being a weaker acid than TPA. Various bases and mixtures thereof are used thereby. The intermediate product is subsequently dissolved in water and filtered, and the TPA is obtained by adding a strong acid.

US patent 2017/0152203 A1 describes depolymerizing PET at temperatures between 20 and 60° C. in mixtures of dichloromethane and methanol. In addition, the use of various further solvents is disclosed in order to subsequently recover TPA and ethylene glycol. The swelling of the polymer, for example by means of nonpolar solvents, is also described. The depolymerizing is performed batchwise, partially for many hours.

German patent 69316545 T2 describes a method for depolymerizing non-coated PET by means of an alkali metal or alkaline earth hydroxide in a kneading extruder. No solvent is thereby added. The mixture is then heated in a kneading extruder and at least partially melted. The alkali metal or alkaline earth terephthalate thus obtained is subsequently dissolved in water and filtered in order to obtain the TPA using sulfuric acid.

In "On-Line Monitoring of Molecular Weight Using NIR Spectroscopy in Reactive Extrusion Process," Bergmann et al. describe the glycolysis of PET in an extruder at a temperature of 320° C. Ethylene glycol is thereby used for depolymerizing the PET. However, no TPA is obtained.

For the methods described above, the conversion of PET predominantly occurs at high temperatures and high pressures. This has the disadvantage that a large amount of apparatus and energy are required and the cost effectiveness of the method is thus reduced. Most of the methods described are also performed only batchwise. Due to the high temperatures and high pressures, the expenditures for heating and pressurization for the batchwise processing provided in the prior art are disadvantageously substantial.

Particularly recycling of multilayered composite materials based on polymers presented very great process challenges due to the material bonding of different materials to the polyalkylene terephthalate. Such composite systems are particularly used as multilayer packaging in the food products industry in order to provide mechanically stable packaging and to provide the protective functions necessary for the food product to be packaged. In order to meet said requirements for packaging, dual- or multiple-layer packaging is used. Said packaging consists of a plurality of layers of various polymers or materials and/or inorganic coatings, each typically having at least one function. For example, ethylene-vinyl acetate copolymer is used as an oxygen barrier in food products packaging. The structure of multilayer packaging systems is described in patent specifications US947525162, U.S. 66/039,261, and EP1036813A1. One popular food product packaging consists of a PET shell coated with a thin layer of polyethylene (PE) or polyamide (PA), for example. Said packaging and the other multilayer packaging feature a permanent material bonding of the various polymers or materials. According to the current prior art, multilayer materials are difficult or nearly impossible to recycle. Patent WO2003104315A1 describes a method for separating multilayer systems, wherein no depolymerizing, dissolving, or oxidizing of the applied material occurs. However, the method utilizes environmentally unfriendly solvents and has not yet been implemented in a cost-effective manner, as far as the authors know. By means of the approach described in patent WO2003070376A1, coated plastic shapes consisting of a PET shape, a barrier layer consisting of polyvinyl alcohol, and a coating layer can be separated by using water. The barrier and intermediate layers consisting of polyvinyl alcohol are dissolved here and the shape can thereby be separated from the coating layer. The method is thereby disadvantageously limited to very specific three-layer systems.

Due to the difficulty of separating the various layers from each other, according to the current state of the art, such multilayer systems or multilayer materials can only be thermally reprocessed or decomposed in landfills after use. In both thermal reprocessing and dumping the waste products in landfills, the material is lost from the material cycle. An overview of the various types of packaging used in the food products industry is provided by Kaiser et al. "Recycling of polymer-based multilayer packaging: a review" in Recycling 2018.

SUMMARY

Considering the background thus described, the object of the present invention is to disclose a method, a device, and a use of the type indicated above for reprocessing waste products comprising substantially polyalkylene terephthalate, particularly polyethylene terephthalate and/or polybutylene terephthalate, in a continuous process by means of depolymerizing, suitable for recycling multilayer systems and colored materials nearly entirely chemically into the starting materials at a high quality level and at a high throughput, in order to be able to produce new polyalkylene terephthalate products from the recycling products without limitation.

The method is a continuous method for the recycling of waste products comprising polyalkylene terephthalate, the waste products being suitably prepared with alkali metal or alkaline earth metal hydroxide and mixed and heated in an extruder or kneading reactor.

The main advantage of the method is that the method allows continuous processing of waste products comprising polyalkylene terephthalate and of multilayer polyalkylene terephthalate. Continuous reprocessing enables the continuous recovery of a recyclable material flow comprising alkali metal or alkali earth metal terephthalate, and the separating and producing of the formed and used alkylene glycol. The recyclable material flow comprising alkali metal or alkali earth metal terephthalate can then be dissolved in a suitable solvent, such as water, then purified, and optionally converted into terephthalic acid (TPA) or a terephthalate acid ester.

Particularly the object relating to a method is achieved by a method of the type indicated above, in that an alkylene glycol is additionally added to the reaction mixture as a reactant, the alkylene glycol being an alkylene glycol produced as a product of the intended depolymerizing, particularly MEG, and no further reactive components being added to the reaction mixture. It has been found in the context of the invention that adding as a reactant an alkylene glycol arising from the subsequent depolymerizing enables optimized processing with respect to recycling rates and recycling quality.

Particularly according to the invention, when reprocessing PET waste products, MEG is added in addition to sodium hydroxide, for example.

In a further advantageous embodiment of the method according to the invention, the waste products are preferably comminuted to a size of no greater than 3 mm prior to producing the reaction mixture. By means of said measure, it is already achieved when producing the reaction mixture, that is, prior to performing the actual depolymerizing, that the waste products, particularly multilayer systems, are mechanically ground and broken up in order to provide the greatest possible surface area for the saponification reaction. The mechanical comminuting damages the material bonds between the various layers and the layers themselves, so that according to the invention a reaction can take place on all or various sides of the waste products, particularly PET.

In a preferred embodiment of the method according to the invention, the alkylene glycol is added at a mass flow rate selected such that the mass flow rate ratio of the waste products to the alkylene glycol is at least 3, particularly 3.3. Said ratio has been found in the context of the invention to be suitable for achieving high throughput rates and high quality of the recycling products obtained.

In a further advantageous embodiment of the method according to the invention, the alkali and/or alkaline earth hydroxide is added at a flow rate such that the stochiometric ratio of alkali and/or alkaline earth hydroxide to polyalkylene terephthalate is at least 2, particularly approximately 2.4, relative to a constitutional repeating unit. A mass flow of 3.33 kg/h of sodium hydroxide can particularly be used for processing a mass flow of 6.66 kg/h of waste products comprising PET.

In a further advantageous embodiment of the method according to the invention, the reaction mixture is transported continuously through a reactor vessel for depolymerizing. A high throughput can be advantageously achieved by means of continually operating. A continuous throughput through a reactor vessel also enables energy-efficient processing, as the reactor vessel can be regulated to a constant temperature.

It is particularly advantageous in the context of the invention if an extruder, particularly a twin-screw extruder, is used for transporting, wherein the screws are preferably co-rotating. The use of a co-rotating twin-screw extruder having tightly intermeshing screw elements advantageously ensures good mixing of the reaction mixture, particularly if sodium hydroxide, for example in pellet form, is used as the alkali or alkaline earth hydroxide. High mechanical stressing of the solid materials is thereby intended.

It is further advantageous in an advantageous embodiment of the method according to the invention if the depolymerizing is performed at a temperature below the decomposition point of the polyalkylene terephthalate and/or below the boiling point of MEG, particularly at 160° C. In comparison with conventional methods working at temperatures between 180° C.-250° C. and above the boiling point of the alkylene glycol produced, that is, at temperatures above 197° C. in the case of PET waste products, energy-saving processing is possible. Because only low pressures are required accordingly, no reactor vessel suitable for high pressures is required for performing the method according to the invention. According to the invention, extruders can particularly be used as reactor vessels. The primary advantage of an extruder according to the invention is the continuous processing and good mixing of the product.

In the context of the method according to the invention, it is advantageous if inert gas, preferably nitrogen, is introduced into the reactor vessel. In place of nitrogen, a noble gas or a mixture of noble gases and/or nitrogen can be introduced in the context of the invention. Said measure prevents oxygen or humidity from entering the reactor vessel, in order to ensure constant dosing. Furthermore, blanketing with inert gas according to the invention advantageously prevents the severely hygroscopic sodium hydroxide from agglutinating and bringing the reaction process to a halt by clogging.

In order to ensure a high rate of recycling at a high throughput, in an embodiment of the invention, the reaction mixture is kneaded and/or mixed and/or transported and/or reverse-transported during the depolymerizing. Particularly in a temporal and/or spatial sequence, a sequence of various kneading, mixing, transporting, and reverse transporting treatments are performed in order to ensure homogenous mixing of the solids and to grind and break up the PET material and the multilayer systems, in turn in order to provide the greatest possible surface area for the saponification reaction. The mechanical stresses damage the material bonds between the various layers and the layers themselves, so that a reaction can advantageously take place on various sides of the PET by means of said processing. By suitably selecting the processing sequence for the reaction mixture, a desired average dwell time of the waste products in the reaction vessel can also be set, for example to 2 minutes.

In a preferred embodiment of the method according to the invention, alkylene glycol is removed from a reaction output, preferably by evaporating. Both the alkylene glycol used as a reactant, such as MEG, and the arising alkylene glycol can indeed be recovered by condensing. This enables particularly efficient processing.

For further processing of the reaction output obtained after depolymerizing, in a preferred embodiment of the method according to the invention, water can be added to the reaction output for dissolving solid components. This can take place in a stirrer vessel or in a mixing screw. The dissolving of the TPA salt obtained by depolymerizing is thereby achieved. When processing waste products comprising PET while adding sodium hydroxide, the adding of water dissolves the disodium terephthalate arising from depolymerizing.

In a further preferred embodiment of the method according to the invention, solids are filtered out of the reaction output. Said solids are particularly insoluble residues, such as PET residues, polyethylene, polypropylene, metals, cardboard, or polystyrene.

In a further advantageous embodiment of the method according to the invention, an acid can then be added to the reaction output in order to convert carboxylate ions formed by depolymerizing and present in the reaction output. To this end, according to the invention, the acid must be stronger than the TPA formed. In this context, sulfuric acid at a concentration of 25% (w/w) is particularly suitable according to the invention.

The object of the invention is also achieved by a device having a reactor vessel comprising conveying means, and having means for feeding a preferably solid alkali and/or alkaline earth hydroxide, and having means for feeding an alkylene glycol into the reactor vessel. Because the device according to the invention comprises a reactor vessel having conveying means, the method can be operated continuously.

If the reactor vessel is temperature-controlled in an embodiment of the invention, then a desired dwell time in the reactor vessel consists possible by means of the conveying means, ensuring high throughput rates at high levels of recycling.

The measure according to the invention, whereby means for infeeding an alkylene glycol such as MEG are provided, enables performing the method according to the invention in a manner proven to be particularly suitable for reprocessing multilayer waste products.

The means for infeeding an alkali hydroxide can comprise a gravimetric metering device having a forced conveyor, for example in order to add solid sodium hydroxide in pellet form. The means for infeeding the hydroxide can also be implemented as a solid material metering device. The means for feeding an alkylene glycol such as MEG can further comprise a gravimetric metering unit. In an embodiment of the device according to the invention, the reactor vessel is implemented as an extruder, particularly a twin-screw extruder, preferably co-rotating. When performing the method, homogenous mixing of the solids can thereby be ensured and the material to be reprocessed, particularly having multilayer systems, can be mechanically ground and broken up in order to provide the greatest possible surface area for the saponification reaction.

In a preferred embodiment of the device according to the invention, the conveying means comprise a screw arrangement having at least one screw element having a ratio of outer diameter to inner diameter of approximately 1.7, particularly 1.66. Said ratio has been found in the context of the invention to be suitable in terms of the quality of reprocessing on one hand, and of the throughput on the other hand.

It has further been found to be advantageous if an embodiment of the device according to the invention has a screw arrangement having a ratio of length to outer diameter of approximately 60. Dwell times of just 2 minutes can thereby be set, within which a very high conversion rate is nevertheless achieved.

In a refinement of the device according to the invention, the conveying means can particularly comprise transporting, kneading, and/or reverse transporting screw elements in order to intermittently convey, knead, or reverse transport the reaction mixture in the reactor. For a suitable sequence of various kneading, mixing, transporting, and reverse transporting elements, homogenous mixing of the solid materials is ensured according to the invention, and the polyalkylene terephthalate material to be processed and the multilayer systems are mechanically comminuted and broken up. This enables the greatest possible surface area for the saponification reaction. The mechanical stressing thereby damages the material bond between the various layers and the layers themselves, so that a reaction can occur from all sides on the polyethylene terephthalate. By suitably combining screw elements, according to the invention, the average dwell time of the waste in the extruder can be set to just approximately 2 minutes, wherein a conversion rate in the range of 92% to 97% can be achieved for depolymerizing in said short reaction time. In the context of the invention, the screw elements can have a length of approximately one to two times the diameter thereof.

According to the invention, the screw elements used can be strung on a shaft in a desired sequence. Spacer discs or transition elements can thereby be used for a change in pitch of the screw elements. Transporting and transport-neutral kneading elements can thereby be used for achieving the greatest possible mechanical stressing and ensuring of an average dwell item of approximately 2 minutes. By using kneading elements according to the invention, energy is advantageously introduced into the reaction mixture and can accelerate the reaction. The kneading elements further ensure good dispersing of the base into the reaction mixture. The use of a reverse-transporting element leads to accumulating of the reaction mixture. A tight gap between the reverse-transporting elements forces the reaction mixture to dwell according to the invention until the waste product residues can be pressed through the gap between elements and the cylinder wall. If some screw elements are implemented according to the invention as transporting mixing elements, then very good mixing is achieved with low shear, said shear less severely mechanically stressing the reaction product than kneading elements.

In an advantageous refinement of the device according to the invention, the reactor vessel has means for controlling temperature in segments adapted to the screw elements. Said measure advantageously makes it possible to select a temperature profile adapted to the particular mechanical process. To this end, individual housing segments of the reaction vessel according to the invention can each be equipped with an individually controlled electric heating and water cooling.

Waste products consisting of polyalkylene terephthalate as dual- or multiple-layer systems having one polymer or a plurality of different polymers and/or natural fibers and/or metal coatings are preferably used for the method according to the invention. The waste products comprising polyethylene terephthalate preferably comprise a layer consisting of polyethylene terephthalate. Examples include typical commercial PET bottles or packaging for food products.

In contrast to the processing of polyalkylene terephthalate waste products in pure form or mixed with other polymers without solvents according to DE 69316545 T2, it is possible by means of the method according to the invention to process coated polyalkylene terephthalate waste products and multilayer systems comprising polyalkylene terephthalate. For particular applications, it is advantageous in the context of the invention if a solvent or a mixture of solvents is added in the extruder or in the kneading reactor. The solvent is thereby preferably selected from the group of alcohols.

By processing the material by means of a solvent and by adding solvent in the depolymerizing process in the extruder or kneading reactor, better mixing, better phase contact, and increased material conversion are ensured and the effectiveness of depolymerizing is increased.

The waste product comprising polyalkylene terephthalate, for example being bottles, film, fibers, shells, automotive interior trim, and other packaging waste products, is comminuted prior to processing according to the invention and is continuously mixed with an alkali metal or alkaline earth hydroxide in a reactor. The reagents are added in a manner such that the alkali metal or alkaline earth hydroxide is present in a stoichiometric amount or a slight stoichiometric excess relative to the constitutional repeating unit of the polyalkylene terephthalate. The reactor used according to the invention can be a continuously operating extruder or kneading reactor.

For the method according to the invention, it can be advantageous to blanket or envelop all of the added reagents and the comminuted waste product comprising polyalkylene terephthalate with an inert gas atmosphere prior to and during processing in the extruder or kneading reactor. Said inert gas atmosphere can consist of nitrogen, noble gases, or mixtures of the same and in particular processes can consist of dry or synthetic air.

For good mixing of the materials, a tightly meshing co-rotating or opposite-rotating twin screw feeder or a multishaft extruder and a kneading reactor having preferably self-cleaning blades can be used in an embodiment of the invention. The arrangement of the extrusion screw elements and the arrangement of the blades is preferably self-cleaning in design and can be adapted to the process by using various mixing, transporting, reverse transporting, and kneading elements.

The extrusion screw elements can be disposed in the method of an embodiment of the invention such that the alkylene glycol produced can be removed at reduced pressure or by means of inert gas flowing thereover. In a preferred embodiment of the invention, the solvent and alkylene glycol vapors can be recovered outside of the reactor by suitable methods, such as condensing.

In a further variant of the method according to the invention, the blades of the kneading mixer can be disposed so as to homogenize the mixture in a self-cleaning manner and the saponification of the polyalkylene terephthalate in the waste product can be performed within 1-60 min. In the present variant according to the invention, an inert gas can flow through the reactor and transport the alkylene glycol vapors out of the reactor. Said vapors can be reprocessed outside of the reactor by means of suitable equipment in the context of the invention.

For the method according to the invention, the reaction product obtained is an alkali metal or alkaline earth terephthalate, an alkylene glycol, and the optionally used solvent. The alkali metal or alkaline earth terephthalate is dissolved in a suitable solvent, preferably water, in the next processing step, filtered, and purified. By means of filtering, the coatings emerging partially unchanged during the method can thus be easily recovered from the multilayer systems. In a concrete example according to the invention, said components can be PE or polyolefin components entering the waste stream in a PE/PET or PP/PET multilayer system as food product packaging.

In contrast to the method according to the prior art, leading to the forming of alkali metal or alkaline earth terephthalates from non-coated PET waste products, the method according to the invention allows processing of waste products comprising coated and multilayer polyalkylene terephthalate and mixtures of various polymers and polyalkylene terephthalate and waste products, and producing valuable alkali metal or alkaline earth terephthalates. TPA can be recovered from the alkali metal or alkaline earth terephthalate obtained in an aqueous solution by adding a stronger acid than TPA.

Developments in the last decade have shown that a recycling capability must be found for large amounts of packaging material. The method according to the invention can provide a solution for a substantial part of the present problem, as particularly bottles or other liquid containers comprising single and multiple layer polyethylene terephthalate can be recycled by means of the method according to the invention, as is not possible according to the state of the art as soon as a direct material bond exists between at least two different materials.

In addition to the direct material bond, the method according to the invention also advantageously tolerates contaminants in the waste products comprising polyalkylene terephthalate, such as additives, fillers, dyes, pigments, encasements, labels, metals, and metal coatings and the like. The contaminants can be separated out in the context of the invention by means of filtering and/or other processing stages, after the reaction products, the alkali metal or alkaline earth terephthalate, have been dissolved in water. The target product, the TPA, is obtained after a purification step by lowering the pH value by means of a stronger acid than TPA.

Application examples of the recycling method are described in greater detail below without being limited thereto.

EXAMPLE 1

In a co-rotating twin-screw extruder having a screw diameter of 18 mm, 0.8 kg/h of PET flakes coated with PE and 0.4 kg/h of sodium hydroxide are added continuously under inert gas atmosphere by means of two metering devices. Said added flows allow a constant weight ratio of PET/NaOH of approximately 2, relative to the constitutionally repeating unit of PET, to be maintained. The extruder housing temperature is set between 160-180° C. The rotary speed of the twin screws is 500 rpm. Sampling the product indicates a PET saponification level of >80%. The MEG arising in the twin-screw extruder is removed by distilling. The solid material thus obtained consists substantially of mono and disodium terephthalate and unreacted PE components. The extruder product is dissolved in water and then subjected to a solid/liquid separation before the solution is purified and the TPA is precipitated by means of a strong acid.

EXAMPLE 2

In the same apparatus as in example 1, using a similar method, a heterogeneous input flow of waste products comprising PET coated with PE and further polymers, particularly polyolefins such as PP, is processed. Approximately 0.8 kg/h of PET flakes coated with PP/PE are present in the input flow, and 0.4 kg/h of sodium hydroxide is introduced into the extruder while adding 0.9 kg/h of separately metered MEG. Said additive flows enable a constant weight ratio of PET to NaOH of approximately 2 to be maintained. The entire apparatus is thereby blanketed with inert gas. The extruder housing temperature is set between 140-160° C. The rotary speed of the twin screws is 400 rpm. Sampling the product indicates a PET saponification level of >90%. The MEG used and produced is removed at reduced pressure in the twin-screw extruder. The solid material thus obtained consists substantially of mono- and disodium terephthalate and unreacted polyolefin components, particularly PP and PE components.

EXAMPLE 3

Using a similar method in a similar apparatus as in Example 1, with a screw diameter of 27 mm, 5 kg/h of PET flakes coated with PE are processed with 2.5 kg/h of sodium hydroxide while adding 5.7 kg/h of MEG. Said additive flows enable a constant weight ratio of PET to NaOH of approximately 2 to be maintained. The extruder housing temperature is set between 140-160° C. The rotary speed of the twin screws is 270 rpm. Sampling the product indicates a PET saponification level of >90%. The MEG used and produced is removed by distilling in the twin-screw extruder. The solid material thus obtained consists substantially of mono- and disodium terephthalate and unreacted PE components.

EXAMPLE 4

In a twin-shaft kneading reactor, 0.8 kg/h of PET flakes coated with PE and 0.4 kg/h of sodium hydroxide are continuously processed while adding 0.9 kg/h of MEG, wherein said additive quantities are metered separately into the twin-shaft kneading reactor, and allow a stoichiometric ratio of NaOH to PET of approximately 2.4, relative to the constitutionally repeating unit of PET, to be constantly maintained. The kneading reactor housing temperature is set between 160-180° C. The rotary speed of the kneading shaft is 500 rpm. Sampling the product indicates a PET saponification level of >80%. The MEG used and produced in the twin-shaft kneading reactor is removed by distilling. The solid material thus obtained consists substantially of mono- and disodium terephthalate and unreacted PE components.

Further features of the invention are listed below.

Feature 1. A method for recycling waste products comprising polyalkylene terephthalate, having the steps:
comminuting the waste products,
feeding the comminuted waste products and an alkali metal or alkaline earth hydroxide into an extruder or into a kneading reactor,
mixing and heating the comminuted waste products with the alkali metal or alkaline earth hydroxide in the extruder or kneading reactor for generating a saponification, and
discharging an intermediate product comprising alkali metal or alkaline earth terephthalate.

Feature 2. The method according to feature 1, characterized in that the waste products comprising polyalkylene terephthalate are dual and/or multilayer systems having a polymer or a plurality of different polymers.

Feature 3. The method according to feature 1 or 2, characterized in that the waste products comprising polyalkylene terephthalate comprise other polymers and/or mixtures of other polymers and/or natural materials and/or metals.

Feature 4. The method according to feature 1, 2 or 3, characterized in that the waste products comprising polyalkylene terephthalate comprise one or more layers of ethylene-vinyl alcohol copolymer (EVOH), cardboard, ethylene-vinyl-acetate copolymer (EVA), polyvinyl alcohol (PVOH), polyamide (PA), polyethylene (PE), polypropylene (PP), polystyrene (PS) or copolymers thereof, along with metals and mixtures thereof.

Feature 5. The method according to any one of the preceding features 1 through 4, characterized in that the waste products comprising polyethylene terephthalate comprise a layer consisting of polyethylene terephthalate.

Feature 6. The method according to any one of the preceding features, characterized in that a solvent or a mixture of solvents is added in the extruder or in the kneading reactor.

Feature 7. The method according to feature 6, characterized in that the solvent is from the group of alcohols, or that the solvent is a nonpolar, halogenated solvent, particularly dichloromethane, chloroform, tetrachloromethane, 1, 2 dichloroethane, or that the solvent is a non-halogenated solvent, particularly dimethyl sulfoxide, or that the solvent is 1,4-dioxane or tetrahydrofuran.

Feature 8. The method according to any one of the preceding features, characterized in that zinc acetate, sodium carbonate, sodium hydrogen carbonate, zinc chloride, and/or lead acetate are added as catalysts for saponification.

Feature 9. The method according to any one of the preceding features, characterized in that the reactive extruding or kneading reacting is performed at temperatures from 100° C. to 180° C., preferably form 140° C. to 160° C.

Feature 10. The method according to any one of the preceding features, characterized in that the reactive extruding or kneading reacting is performed continuously and while blanketed with inert gas, particularly argon/nitrogen, for a dry and oxygen-free atmosphere.

Feature 11. The method according to any one of the preceding features, characterized in that the alkylene glycol produced by saponification is separated by distilling.

A preferred embodiment of the invention is described as an example with reference to a drawing, wherein further advantageous details can be seen in the figures of the drawing.

Functionally identical parts are thereby labeled with the same reference symbol.

BRIEF DESCRIPTION OF THE DRAWING

FIG. 1 shows a block flow diagram for illustrating the method steps of an embodiment of the method according to the invention.

DETAILED DESCRIPTION

The preferred embodiment of the method according to the invention described with reference to FIG. 1 enables recycling of polyethylene terephthalate (PET) waste products previously unable to be recycled, or recycled only thermally. The method can also be used for recycling other polyalkylene terephthalates such as polybutylene terephthalate.

Waste products comprising PET, including multilayer systems, such as beverage bottles, detergent bottles (opaque, clear, or dyed black) or food product packages of other types, such as salad shells, sausage and cheese packaging, or production waste comprising PET, are washed in a first step 1 and comminuted to smaller than 3 mm. The waste products are then optionally pre-dried in a second step 2 in order to reduce the water content of the PET material. Alternatively, the material to be processed can be pre-dried after the method according to the invention. In this case, the step 2 of drying after step 1 of comminuting can be eliminated. For particular applications according to the invention, however, further, more intensive drying 2 can be advantageous.

In a further process step of "depolymerizing" 3, the waste products are fed into a co-rotating twin-screw extruder having tightly meshing screw elements. The saponification and depolymerization of the PET is performed continuously in the extruder. In the system described as an example with reference to FIG. 1, 6.66 hg/h of waste products comprising PET, 3.33 kg/h of sodium hydroxide, and 2 kg/h of MEG are processed in the extruder. The ratio of sodium hydroxide to PET waste products is set during the process according to the invention so that a constant stoichiometric ratio of approximately 2.4 is set relative to the constitutionally repeating unit of PET. The reaction output of the extruder comprises disodium terephthalate, MEG, and nonreactive components of the sodium hydroxide and the PET waste, such as PET residues, dyes, products of decomposition of PA and dyes, and other polymers such as PE, PP, and PS.

The twin-screw extruder is modular in construction and comprises 14 temperature zones. The housings are each equipped with an individually controlled electric heater and water cooling. The ratio of the outer screw diameter Da to the inner screw diameter Di is a characteristic parameter for the potential free volume of the screw. For the extruder used here, the Da/Di ratio of the screw elements is 1.66. The ratio of the screw length L to the diameter of the screw D describes the processing length of the extruder and is 60 for the present extruder. The screw geometry is modular in structure and can be adapted to the process and the PET material. The extruder comprises the following individually temperature-controlled cylinders:

Cylinder 1: main intake, Cylinder 2: top injection nozzle, Cylinder 3: side outgassing with reverse flow, Cylinder 4: side infeed of sodium hydroxide, Cylinder 5: top injection nozzle, Cylinder 6: top venting ports, Cylinder 7: closed, Cylinder 8: top injection nozzle, Cylinder 9: side outgassing with reverse flow, Cylinder 10: closed, Cylinder 11: outgassing, Cylinder 12: closed, Cylinder 13: outgassing, Cylinder 14: injection nozzle, Cylinder 15: transport, output after cylinder 15. In cylinders 1 through 15, the reactants are thus first drawn into the extruder and mechanically processed in the apparatus while passing through all zones. In the last, that is, the fifteenth, cylinder, the product is transported out of the extruder. The output is implemented as an opening through which the product is transported out of the apparatus.

The apparatus is equipped with up to three pressure sensors inserted in the cylinder opening of the injection nozzle. The housings/cylinders 2 through 15 are temperature-controlled to 160° C. Cylinder 1 is not temperature-controlled. The rotary speed of the co-rotating twin screws is set to 100 rpm.

The screw configuration is selected so that good mixing of the two solid materials can be ensured in the process. The screw elements used can be strung on the shaft in an arbitrary sequence. When the number of threads of the screw elements changes, spacer discs or transition elements are used. In order to achieve the highest possible deformation and mechanical stressing and a relatively high average dwell time of approximately 2 minutes of the multilayer PET waste products, transporting and transport-neutral kneading elements are used in the design of the screw configuration. Furthermore, by using kneading elements according to the invention, energy is introduced into the reaction mixture and can accelerate the reaction. Furthermore, kneading elements further ensure good dispersing of the base in the reaction mixture. The use of a reverse-transporting element leads to accumulating of the reaction mixture. A tight gap between the reverse-transporting elements forces the reaction mixture to dwell until the PET waste product residues can be pressed through the gap between elements and the cylinder wall. In the region of outgassing and atmospheric opening, screw elements having a high free screw volume are used. This allows solvent to be continuously removed from the reaction mixture. Furthermore, a series of transporting mixing elements are installed in the screw configuration and mechanically stress the reaction product less than the kneading elements due to lower shear, but do ensure very good mixing.

In the region of cylinder 1, the PET is metered gravimetrically by means of a solid metering device. The material is transported into the extruder via the intake and the screw elements having a large free screw volume and is warmed therein. In cylinder 1 itself, however, only transporting occurs, but no temperature control. In cylinder 2, MEG is added via the top filling opening by means of a gravimetric metering device. Solid sodium hydroxide in pellet form is added gravimetrically via a side metering device in cylinder 4 and via a second metering device by means of a forced feeder. Cylinder 4 further comprises an atmospheric opening. Both the solid metering device for the PET and the solid metering device for the sodium hydroxide are blanketed with inert gas in order to prevent inflow of oxygen and moisture and to ensure constant metering. Without inert gas blanketing, the highly hygroscopic sodium hydroxide would very quickly agglutinate and clog, causing the process to come to a halt. The MEG used and the MEG forming due to condensation can be recovered via an atmospheric opening in cylinder 6 and cylinder 10.

The screw configuration is shown in Table 1. The angle values indicated refer to the angle between the discs of the kneading elements in each case. A sequence of various kneading, mixing, transport, and reverse transport elements is used for ensuring homogeneous mixing of the solids and for mechanically grinding and breaking up the PET material and the multilayer systems in order to provide the greatest possible surface area for the saponification reaction. The mechanical stresses damage the material bonds between the various layers and the layers themselves, so that a reaction can advantageously take place on various sides of the PET by means of said processing. In contrast thereto, without mechanical stressing, the base would attack only the exposed PET surfaces and PET edges of the PET flakes coated on one or more sides. By selecting the screw configuration shown, the average dwell time of the PET waste product in the extruder is set to approximately 2 min. Within said reaction time, conversion of the PET content of the PET waste product occurs at 92-97%.

the invention, particularly multilayer PET waste products can be converted efficiently at a high throughput and high quality and made into starting materials available for polymerization without limitation for reprocessing, that is, for producing polyalkylene terephthalates. Part of the alkylene glycol thus produced can thereby be used in the reverse flow for depolymerizing in the method according to the invention.

What is claimed is:

1. A method for reprocessing waste products containing polyalkylene terephthalate, the method comprising the steps of:
   depolymerizing the waste products in a continuous process, the continuous process being performed in a twin-screw extruder,
   the depolymerizing including adding a solid alkali hydroxide and/or solid alkaline earth hydroxide to the waste products to produce a reaction mixture, the reaction mixture consisting of the waste products and the solid alkali hydroxide and/or solid alkaline earth hydroxide,
   adding an alkylene glycol to the reaction mixture as a reactant, wherein the alkylene glycol is an alkylene glycol produced as a product of the depolymerizing, wherein no further reactive components are added to the reaction mixture,

TABLE 1

| Screw configuration for PET depolymerizing | | | | | | | | |
|---|---|---|---|---|---|---|---|---|
| Cylinder | 1 | 2 | 3 | 4 | 5 | 6 | 7 | 8 |
| Screw configuration | PET intake | Outgassing, | MEG intake | NaOH intake | Transport Kneading (45°) | Reverse transport | Transport Kneading (45°) | Kneading (90°) |
| Cylinder | 9 | 10 | 11 | 12 | 13 | 14 | | |
| Screw configuration | Transport | Mixing | Outgassing | Kneading (45°) | Mixing | Transport | Transport | |

The paste-like reaction output is granulated, comminuted, and loaded onto a temperature-controlled conveyor having extraction in the subsequent step "post-treatment" 4. The MEG vapors are condensed and collected at a cooler.

In the subsequent method step "dissolving" 5, the reaction output is dissolved in water in a stirrer vessel or a mixing screw (55 kg/h, 133 g/L solubility of the disodium terephthalate). The insoluble residues (PET residue, PE, PP, metals, PS, cardboard) are separated out by filtering 6.

After filtering 6, in a method step "purifying" 11, contaminants and byproducts of the method are separated out. In the context of the invention, various methods are conceivable here and are per se known to the person skilled in the art.

In the subsequent method step "precipitating TPA" 7, sulfuric acid (9.6 kg/h, 25% (w/w)) is added to the solution. The precipitated TPA is obtained by filtering 8 and washing 9 with water and is filtered out. The TPA is washed with water in order to remove residues of the sulfuric acid and the sodium sulfate formed during precipitating.

After washing 10, separating of solid and liquid 10 takes place in order to separate the solid TPA, being insoluble in water, from the washing water.

By means of the method according to the invention, the device according to the invention, and the use according to wherein the twin-screw extruder is used for transporting the reaction mixture during the depolymerizing, the screws of the twin-screw extruder are co-rotating, and the transporting of the reaction mixture includes at least one of kneading, mixing, conveying, and reverse conveying the reaction mixture by the twin-screw extruder such that an average dwell time of the reaction mixture in the twin-screw extruder of no greater than 2 minutes is achieved.

2. The method according to claim 1, wherein the waste products are comminuted to a size of no greater than 3 mm prior to producing the reaction mixture.

3. The method according to claim 1, wherein the alkylene glycol is added at a mass flow rate selected such that the mass flow rate ratio of the waste products to the alkylene glycol is at least 3.

4. The method according to claim 1, wherein the solid alkali hydroxide and/or solid alkaline earth hydroxide is added at a mass flow rate such that the ratio of solid alkali hydroxide and/or solid alkaline earth hydroxide to the polyalkylene terephthalate is approximately stoichiometric relative to a constitutional repeating unit.

5. The method according to claim 1, wherein the reaction mixture for depolymerizing is transported continuously through the twin-screw extruder.

6. The method according to claim 1, wherein the depolymerizing is performed at a temperature below the boiling point of the polyalkylene terephthalate and/or below the boiling point of a monoethylene glycol.

7. The method according to claim 1, wherein the reaction mixture for depolymerizing is transported continuously through the twin-screw extruder, and inert gas is fed into the twin-screw extruder.

8. The method according to claim 1, wherein alkylene glycol is removed from a reaction output.

9. The method according to claim 1, wherein water is added to a reaction output for dissolving solid components.

10. The method according to claim 1, wherein solids are filtered out of a reaction output.

11. The method according to claim 1, wherein an acid is added to a reaction output in order to convert carboxylate ions formed by depolymerizing and present in the reaction output into acids.

12. The method according to claim 1, wherein the polyalkylene terephthalate is polyethylene terephthalate and/or polybutylene terephthalate, the solid alkali hydroxide and/or solid alkaline earth hydroxide includes sodium hydroxide, and the alkylene glycol is mono-ethylene glycol (MEG).

13. The method according to claim 3, wherein the mass flow rate ratio of the waste products to the alkylene glycol is approximately 3.3.

14. The method according to claim 4, wherein the stoichiometric ratio of the solid alkali hydroxide and/or solid alkaline earth hydroxide to polyalkylene terephthalate is approximately 2.4 equimolar.

15. A method for reprocessing waste products containing polyalkylene terephthalate, the method comprising the steps of:
    depolymerizing the waste products in a continuous process, the continuous process being performed in a twin-screw extruder,
    the depolymerizing including adding a solid alkaline earth metal hydroxide to the waste products to produce a reaction mixture,
    adding an alkylene glycol to the reaction mixture as a reactant, wherein the alkylene glycol is an alkylene glycol produced as a product of the depolymerizing, no further reactive components are added to the reaction mixture, and the reaction product includes an alkaline earth metal terephthalate,
    the twin-screw extruder is used for transporting the reaction mixture during the depolymerizing, the screws of the twin-screw extruder are co-rotating, and
    the transporting of the reaction mixture includes at least one of kneading, mixing, conveying, and reverse conveying the reaction mixture by the twin-screw extruder such that an average dwell time of the reaction mixture in the twin-screw extruder of no greater than 2 minutes is achieved.

* * * * *